United States Patent [19]

Raible

[11] Patent Number: 5,266,265
[45] Date of Patent: Nov. 30, 1993

[54] MODULAR DISPOSABLE BLOOD OXYGENATOR/HEAT EXCHANGER WITH DURABLE HEAT SOURCE COMPONENT, SELECTIVELY INCLUDING ROTARY OR VENTRICULAR BLOOD PUMP, VENOUS RESERVOIR, AND AUXILIARY HEAT EXCHANGE COMPONENT

[75] Inventor: Donald A. Raible, Santa ana, Calif.

[73] Assignee: Baxter International, Inc., Deerfield, Ill.

[21] Appl. No.: 958,667

[22] Filed: Oct. 8, 1992

[51] Int. Cl.⁵ .............................................. A61M 1/14
[52] U.S. Cl. ...................................... 422/46; 422/45; 422/48; 210/321.6; 210/321.8
[58] Field of Search ............... 422/45, 46, 47, 48; 210/321.6, 321.8

[56] References Cited

U.S. PATENT DOCUMENTS

| | | | |
|---|---|---|---|
| 4,065,264 | 12/1977 | Lewin | 422/46 |
| 4,094,792 | 6/1978 | Bentley | 210/321 B |
| 4,138,288 | 2/1979 | Lewin | 422/46 |
| 4,138,464 | 2/1979 | Lewin | 422/46 |
| 4,158,693 | 6/1979 | Reed et al. | 422/46 |
| 4,180,896 | 1/1980 | Reed et al. | 422/46 |
| 4,196,075 | 4/1980 | Bentley | 210/19 |
| 4,440,723 | 4/1984 | Gordon | 422/47 |
| 4,533,516 | 8/1985 | Johnson et al. | 422/46 |
| 4,645,645 | 2/1987 | Martinez et al. | 422/46 |
| 4,698,207 | 10/1987 | Bringham et al. | 422/46 |
| 4,876,066 | 10/1989 | Bringham et al. | 422/46 |
| 4,948,560 | 8/1990 | Deguchi et al. | 422/48 |
| 5,017,103 | 5/1991 | Dahl | 417/420 |
| 5,124,127 | 6/1992 | Jones et al. | 422/46 |

Primary Examiner—James C. Housel
Assistant Examiner—N. Bhat
Attorney, Agent, or Firm—Kurt MacLean; Raymond Sun

[57] ABSTRACT

A blood oxygenator/heat exchanger system includes disposable and durable components, the latter being possible of permanent installation to further reduce costs, inconvenience and risks of use. The system may selectively include a blood pump of axial, centrifugal, or ventricular type, along with an integral venous reservoir. By combination, arrangement and cooperation of structural features blood pumping volume is decreased, advantageous blood flow paths are achieved, blood damage is reduced, and durable components are reusable for lowest costs. The oxygenator/heat exchanger nests upon a durable heat source base to be supported thereby, while redundant boundaries are provided between blood and heat transfer media.

39 Claims, 8 Drawing Sheets

MODULAR DISPOSABLE BLOOD OXYGENATOR/HEAT EXCHANGER WITH DURABLE HEAT SOURCE COMPONENT, SELECTIVELY INCLUDING ROTARY OR VENTRICULAR BLOOD PUMP, VENOUS RESERVOIR, AND AUXILIARY HEAT EXCHANGE COMPONENT

BACKGROUND OF THE INVENTION

1. Field Of The Invention

The present invention relates to a blood oxygenator and temperature control apparatus. More specifically, the present invention relates to a blood oxygenator forming a disposable component of a heat exchanger having as its other component a durable heat source member. The two components are unitable in heat exchange relation. Alternatively, the blood oxygenator may also include any one or all of a blood pump, venous reservoir or auxiliary heat exchange component.

2. Description of the Related Art

Extracorporeal blood oxygenation systems are well known for pumping and/or oxygenating a patient's blood during cardiovascular surgery or other procedures. The blood oxygenation system replaces or supplements the normal physiological lung function of replacing the carbon dioxide in venous blood with oxygen for the arterial blood system. The blood oxygenator typically includes a venous reservoir, a heat exchanger, a blood pump and a blood oxygenator. The venous reservoir provides a supply of venous blood to be oxygenated, the heat exchanger maintains the blood temperature at the "normal thermic" temperature or at a sub-normal temperature, depending on the procedure, the blood pump provides blood transport from the venous reservoir (or other source such as venous blood tubing) to an oxygenator input, through the oxygenator and to the output for return to the patient, and the oxygenator provides a suitable membrane for exchange of carbon dioxide for oxygen.

Some prior blood oxygenation systems, such as that described by Bringham et al., U.S. Pat. No. 4,698,207, integrated several of the major components of the blood oxygenation system, namely the venous reservoir, the heat exchanger and the oxygenator. Such an integrated system, while permitting placement close to the patient may still require a substantial volume of priming blood or fluid. Of course, the prior oxygenator systems with separate blood pump and connecting conduits required even more priming blood or fluid volume. Furthermore, the increase in blood volume within the extracorporeal circuit undesirably increases the volume of blood and/or blood products which must be administered by transfusion during the procedure. A large priming volume increases the amount of non-physiologic matter with which the blood contacts as the blood travels through the blood oxygenation system, thereby increasing the potential for mechanical, chemical and/or immunoreactive damage to the blood. Non-blood priming solutions also cause hematocrit dilution. A large priming volume increases blood-wetted surface area which must be treated with antithrombolytic compounds, such as heparin, and also can increase hemolysis (blood damage). Also, a large priming volume ordinarily means a significant volume of blood is not reinfused to a patient at the conclusion of a surgical procedure.

In the oxygenator, a bundle of hollow oxygenation membrane fibers provide the transport mechanism for the oxygen/carbon dioxide exchange. The fibers are formed from gas permeable membrane material allowing the oxygen to permeate through to the venous blood being pumped past the fiber exteriors while carbon dioxide permeates in the opposite direction. Necessarily, patient blood comes into contact with the oxygenator surfaces, requiring disposal after use.

With prior blood oxygenator systems having separate components, for example, separate venous reservoir, blood pump, oxygenator, and heat exchanger, a large number of component parts, and interconnecting conduits must be assembled. This multiplicity of components presents a high cost, assembly time burden, chance for error, plural leakage paths and contamination vectors, and added clutter and complexity in the operating room. Skilled attention must also be paid upon disassembly of the system to avoid blood contact, and to properly identify and separate durable from disposable components.

In view of the above, a need is recognized for a blood oxygenating system utilizing, to the extent desired or practicable, a combination of durable and disposable components integrating a disposable blood oxygenator/heat exchanger with minimum priming volume and blood-wetted surface area, decreased blood damage and opportunity for foreign surface contact and contamination entry, all with a durable heat source component. Reuse of the heat source component of the heat exchanger would provide a safer oxygenator system. Because the oxygenator/heat exchanger component and the heat-source heat exchanger component would be separate parts each with their own fluid boundary walls, double or redundant boundary wall separation between blood and heat transfer media (water, perhaps) would be provided by the oxygenator/heat exchanger.

Further to the above, a need is recognized to further advantageously combine the above-described oxygenator/heat exchanger with a blood pump also having durable and disposable components in unit with the durable and disposable components, respectively, of the oxygenator/heat exchanger. Those skilled in the pertinent art will quickly recognize the increased ease and convenience of use and decreased costs of manufacture and use associated with such a combination. Importantly, the risks of error in set up, contamination paths, leak paths, and priming volume are all potentially reduced by such a combination. Thus, and further to the above, the need is recognized for such a combination also integrating a venous reservoir integrated with the disposable components of the system so that a detached hard or soft reservoir need not be employed. Of course, each such successive step of integration potentially offers incremental improvement of the advantages outlined above.

SUMMARY OF THE INVENTION

The present invention provides a blood oxygenator/heat exchanger having a disposable oxygenator/heat exchanger component and a durable heat-source component cooperable therewith, and which can be permanently connected to a heat source, for example, to a hot water supply, if desired. The blood oxygenator/heat exchanger component defines an elongated annular body defining radially inner and radially outer wall surfaces available for heat transfer. An annular oxygenator cavity defined within the oxygenator/heat exchanger component provides both a desired blood-contact surface area of $O_2/CO_2$ permeable gas-exchange membrane and adequate heat transfer surface area while requiring a minimal blood-priming volume.

According to an alternative embodiment, the present invention provides a disposable oxygenator/heat exchanger component cooperable with a durable heat source component wherein the disposable and durable components also incorporate respective portions of a rotary blood pump so integrated therewith as to further realize the advantages potential in the present invention.

Yet a further alternative embodiment of the present invention provides a reciprocable ventricular pump providing pulsatile blood flow. By advantageous combination, arrangement and cooperation of the structural features of the present invention such a ventricular pump is provided with disposable and durable portions and with only an inlet check valve (not requiring an outlet check valve). A gravity impelled downward columnar flow of blood in the oxygenator/heat exchanger communicating with the pump discharge advantageously provides a sufficient negative relative pressure head to effect pump operation without an outlet check valve. Thus, the advantages of decreased blood damage are further realized by the present invention.

Still further, another alternative embodiment of the invention integrates a disposable venous reservoir with a disposable oxygenator/heat exchanger and blood pump as described above to further realize the advantages potential in the present invention. The durable heat source component is cooperable in like manner with this and the other embodiments disposable components.

Finally, by advantageous selection and commonality of the combination, arrangement and cooperation of structural features employed in the various invention embodiments a modular blood oxygenator/heat exchanger, blood pump, and venous reservoir system is provided which allows selection of the degree of system integration desired while always allowing use of substantially the same durable heat source component. Because of this integrity of system design, each of the alternative embodiments may also selectively utilize an alternatively durable or disposable auxiliary heat source component in those circumstances indicating a need for an increased rate of heat exchange with the treated blood. As will be seen, at the expense of only a slight increase in cost and complexity, the heat exchange capacity of the system is substantially doubled with no change in blood priming volume, blood-wetted surface area, or any other loss of the significant and plural advantages realized by the present invention.

In accordance with the present invention, a reusable blood oxygenator/heat exchanger for a blood oxygenation system includes a heat source or thermal supply at a temperature differential relative to the blood temperature. The heat source component defines a heat exchange surface for contacting a corresponding heat exchange surface on a blood oxygenator component placed in heat exchange contact therewith wherein the heat exchange surfaces are shaped so as to nest together In one form of the invention, the heat exchange interface is substantially cylindrical in plan view and is slightly conical tapering from bottom to top to allow close contacting engagement between the corresponding outer surface of the heat source component and the inner surface of the blood oxygenator component.

Further, the reusable heat source component may form a base on which the integrated components of the blood oxygenation system may be mounted and supported during a surgical procedure. The heat source component may also form part of a stable mounting assembly which may remain permanently connected to the heat exchange medium (heated, ambient, or chilled water, for example), thereby simplifying the connection of external supply lines such as blood supply tubes and the like. A reusable heat source component which forms an integral base also forms a more convenient unit which need not be disassembled or separately handled after each use. By having its own base with permanently attached water supply, the heat source component does not need to be handled directly during or after a procedure, thereby reducing the possibility of water leakage.

BRIEF DESCRIPTION OF THE DRAWINGS

FIGS. 7, 7A, and 7B in conjunction depict yet another alternative blood oxygenator system according to the present invention and including a blood oxygenator/heat exchanger, heat source, blood pump, integral venous reservoir, and optional auxiliary heat source component.

DETAILED DESCRIPTION OF THE PREFERRED EMBODIMENTS

Figure 1:
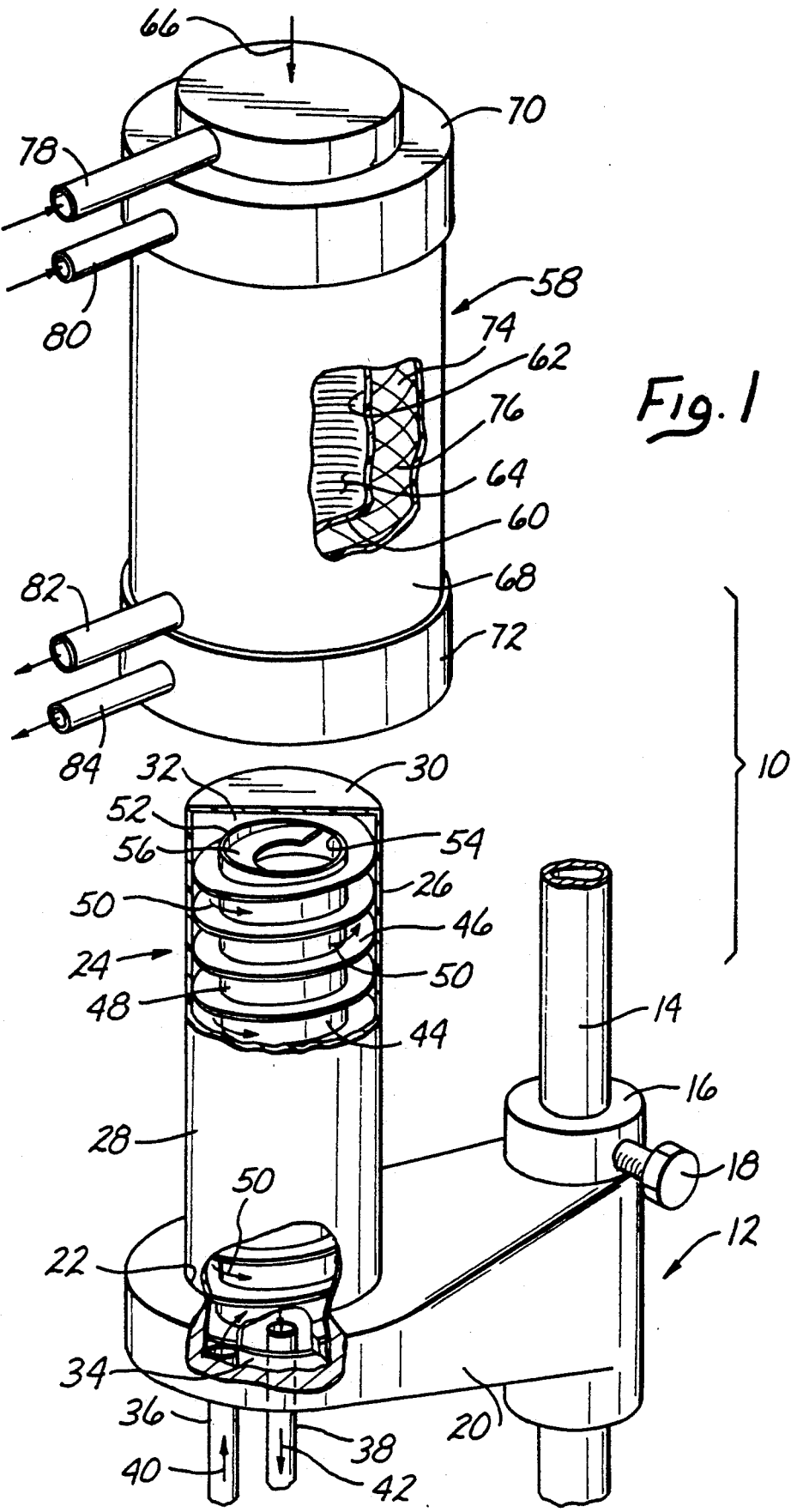
FIG. 1 is a somewhat schematic perspective view exploded and partially cutaway to depict salient features of a blood oxygenator/heat exchanger component above a cooperable heat source component according to one embodiment of the present invention.

In order to introduce the reader to the general concept of the present invention, FIG. 1 schematically depicts a blood oxygenator system, generally referenced with the numeral 10. In order to support the oxygenator 10, a conventional stand 12 having a vertically extending column 14, only a fragment of which is visible viewing FIG. 1, is employed. The oxygenator 10 includes a bracket member 16 removably and adjustably secured to column 14 by means of a thumb screw 18 threadably engaging the bracket 16, and the inner end of which cinches against the outer surface of column 14. Bracket member 16 includes a laterally extending arm portion 20 defining a vertically extending through aperture 22.

Received at its lower portion in the aperture 22 and extending vertically upwardly from arm 20 is a durable heat source component, generally referenced with the numeral 24. The heat source component 24 includes an outer wall 26 having an outer surface 28 which appears generally cylindrical, but which is actually frustoconical with a slight increase in diameter in the downward direction, viewing FIG. 1. Outer wall 26 includes an integral end wall portion 30 which in conjunction with the wall portion 26 bounds a chamber 32 therein. A closure member 34 completes the boundary of chamber 32 and provides downwardly extending hose nipples 36,38 accessible from the underside of arm 20 whereby an inflow and outflow of heat exchange liquid may flow through the chamber 32, as depicted by arrows 40 and 42. Within the chamber 32, a tubular flow guide member 44 includes a helical fin 46 extending radially outwardly toward engagement with wall 26. This fin 46 defines a helically extending liquid flow passage 48 communicating with fluid inflow 40 and extending circumferentially and upwardly as depicted by flow arrows 50. At an upper end 52 of guide member 44, liquid flows between passage 48 and an inner bore 54 of the guide member 44. Within the guide member 44 a similar helical fin 56 extends radially inwardly to guide liquid flow helically downwardly to exit via nipple 38, as depicted by arrow 42.

At this point, it is well to point out that while throughout this disclosure the member 24 is referred to as a "heat source" component, those skilled in the pertinent art will appreciate that cool or even chilled liquid may be circulated in chamber 32. The direction of heat transfer to or from the heat exchange liquid makes no difference to understanding the present invention. Indeed, those skilled in the art will appreciate that during some surgical procedures patient hypothermia (by blood cooling) is desired, followed by blood warming to facilitate return of the patient to normal body temperature.

FIG. 1 also depicts an elongate disposable annular blood oxygenator/heat exchanger component 58. Component 58 includes an inner frustoconical wall 60 defining a downwardly open bore 62. The bore 62 tapers upwardly from its open lower end (not visible in FIG. 1) to define a frustoconical inner surface 64 matching and cooperably engageable with the surface 28 in heat exchange relation therewith when component 58 is supportably received upon component 24, as depicted by arrow 66. Component 58 also includes a cylindrical outer wall 68 which in combination with an upper closure member 70 and an annular lower closure member 72 bound an elongate annular chamber 74.

Chamber 74 receives an elongate annular membrane oxygenation module 76. Preferably, module 76 is formed of helically wound single or multiple strand hollow permeable membrane fibers. As is well known to those skilled in the pertinent art, this fibrous membrane structure facilitates exchange of oxygen for carbon dioxide in blood. Communicating with the module 76, the component 58 also includes a blood inlet 78, an oxygen inlet 80, a blood outlet 82, and an outlet 84 for vitiated oxygen (including $CO_2$ and moisture). Importantly, the outlet 84 is at the very bottom of the chamber 74 so that any moisture which permeates the membrane module 76 is flushed from the oxygenator 10.

When the component 58 is received removably upon component 24, the surfaces 28 and 64 engage one another in heat exchange relation and substantially without an air gap therebetween because of their matching frustoconical tapers. Thus, the heat source member 24 is insulated from ambient by the oxygenator component 58, and heat transfer between the fluid in chamber 32 and blood in chamber 74 readily occurs through the engaged walls 26 and 60. On the other hand, those skilled in the art will quickly appreciate that the separate walls bounding chambers 32 and 74 provide redundant sealing separation between the heat exchange fluid and blood. That is, the liquid-tight integrity of the heat source component may be verified before surgery, if desired, by pressurizing the chamber 32 without oxygenator 58 in place. Leak-free operation of component 24 is easily verified visually, prior to setting the oxygenator component 58 in place (arrow 66). However, even if a leak of the heat source component were to develop during surgery, blood contamination from this source is not likely because of wall 60 further separating the heat exchange medium from blood. Oxygenator 58 requires a relatively small blood priming volume, and the priming and interconnecting volumes of a separate heat exchanger are entirely eliminated. Following surgery, the component 58 is discarded while heat source component 24 is reusable.

Figure 2:
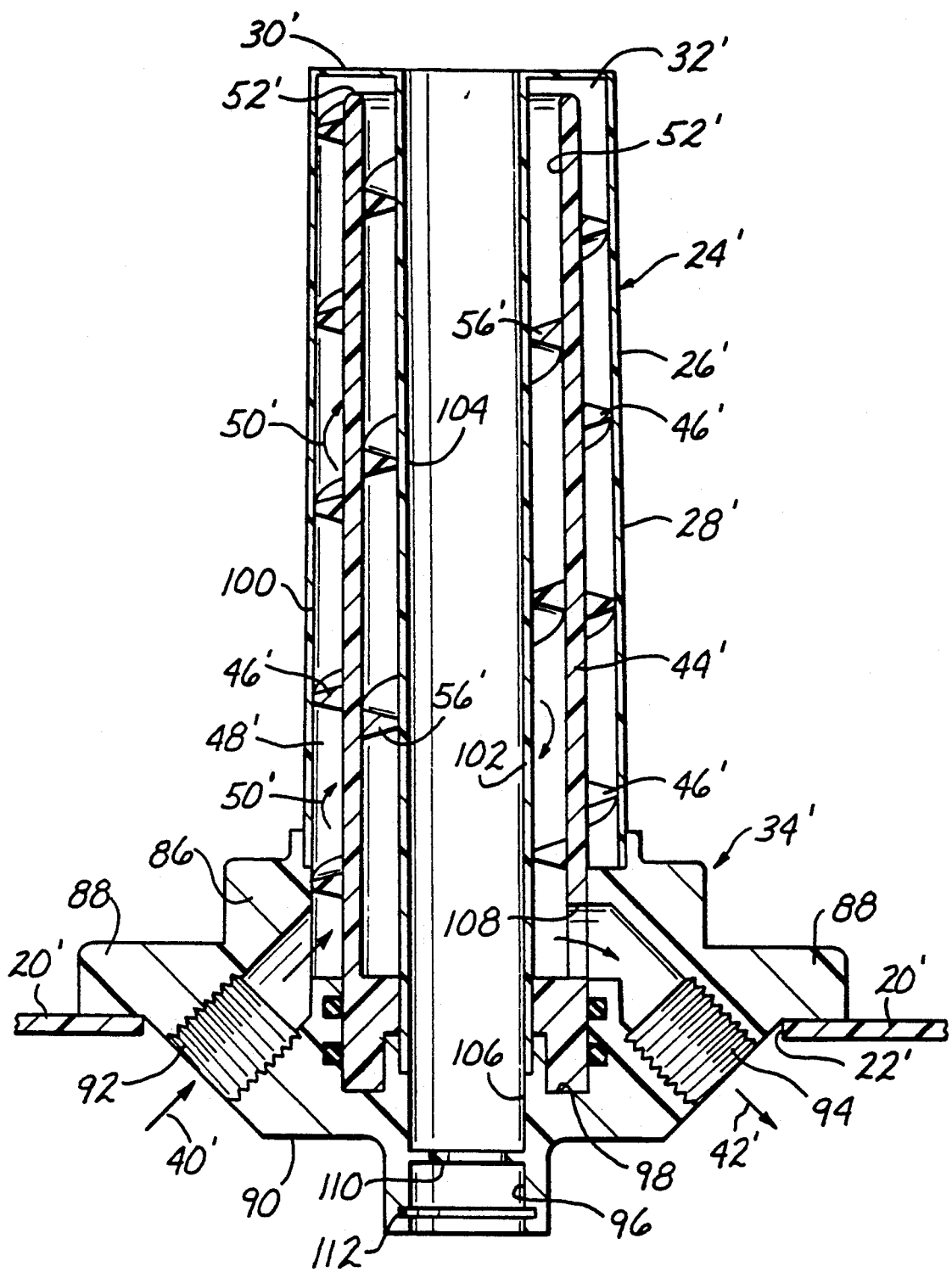
FIG. 2 is a side-sectional view of an exemplary heat source component.
Figure 3:
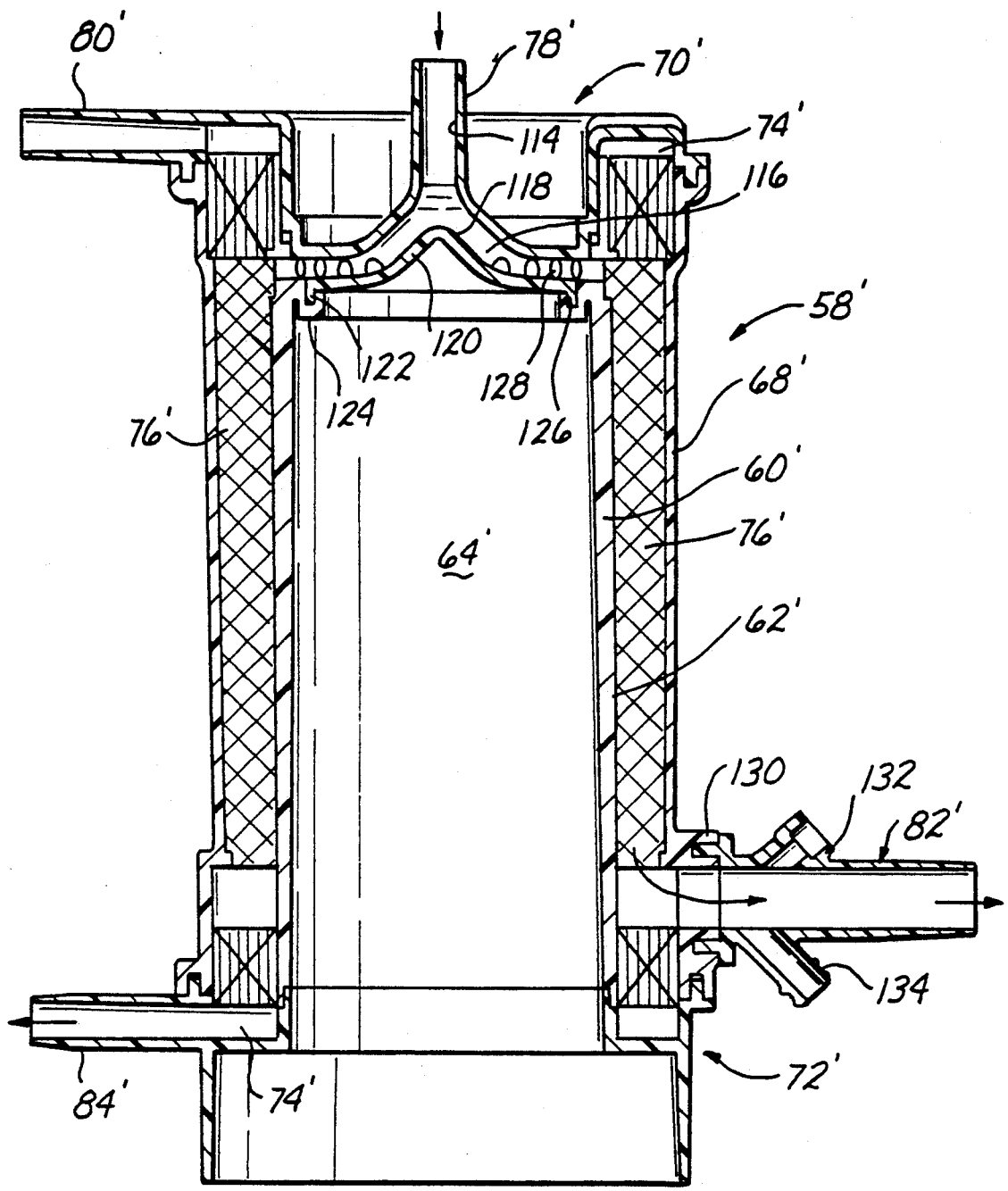
FIG. 3 is a side-sectional view of an exemplary blood oxygenator/heat exchanger component.

Turning now to FIGS. 2 and 3 in conjunction, cross-sectional detailed views of an embodiment of this invention similar to that schematically depicted in FIG. 1 are provided. Features of FIGS. 2 and 3 analogous in structure or function to those depicted and described by reference to FIG. 1 are referenced with the same numeral used earlier and having a prime added thereto.

Viewing FIG. 2, it will be seen that durable heat source component 24' includes a closure member 34' which takes the form of a base 86 having a flange portion 88 engageable with the arm 20' and a lower portion 90 extending downwardly through the aperture 22' to define threaded inlet and outlet ports 92, 94, respectively. Flange 88 is secured to arm 20' by fasteners, not visible in FIG. 2. The base 86 defines a stepped vertically extending through bore 96, including an annular upwardly disposed recess 98. Sealingly disposed in the bore 96 is an elongate annular cup-like member 100 which outwardly defines the heat source component 24' with wall 26' and heat exchange surface 28'. However, the cup-like member 100 also includes a radially inner elongate annular wall 102 defining a central bore 104 aligned with and forming a continuation of a smaller-diameter bore portion 106 of bore 96. An annular end portion 30' spans radially between walls 26' and 102 to close the upper end of the cup-like member 100. Disposed in the recess 98 and extending upwardly in the chamber 32' between the walls 26' and 104 is an annular flow guide member 44'. The annular outer space between flow guide 44' and wall 26' communicates with inlet port 92, while the inner annular space between guide 44' and wall 102 communicates via a passage 108 with outlet port 94. Base member 96 also includes an inwardly extending locating collar 110 and associated retention groove 112 on bore 96, the importance of which will be further explained.

Turning now to FIG. 3, a disposable blood oxygenator component 58' cooperable with heat source component 24' in supported and heat exchanging relationship is depicted. The oxygenator component 58' includes an upper closure member 70' which is somewhat cup-shaped and defines a central blood inlet 78'. The blood inlet 78' defines a central descending passage 114 leading to a circular distribution chamber 116 defined between the member 70' and the upper surface 118 of a closure member 120. Closure member 120 at a circumferential peripheral edge portion 122 thereof sealingly cooperates with an annular rim part 124 of wall 60' which defines an annular recess 126 for receiving the edge portion 122. Chamber 116 leads to a circumferential plurality of transfer ports 128 defined by wall 60' and opening radially outwardly therethrough from chamber 116 to chamber 74' and membrane module 76'. Outer wall 68' defines a spigot 130 opening to and sealingly cooperating with outlet 82'. Preferably outlet 82' also includes a blood sampling port 132 and a blood temperature probe fitting 134.

Importantly, those skilled in the pertinent art will recognize that the total priming volume of oxygenator 58', essentially the total volume of chamber 116, and outlet 82', along with membrane module 76', is only very little more than the essential volume of the membrane module 76' itself. In other words, the disposable oxygenator/heat exchanger module 58' by its favorable combination, arrangement and cooperation of features provides a small priming volume, and the priming volume of a separate heat exchanger and interconnecting tubing is entirely eliminated. Also, the oxygenator 58' provides an advantageous gravitational downward flow of blood from inlet 78' and particularly from ports 128 through the module 76' and to outlet 82'. As will be seen, this blood flow arrangement has additional potential advantages which may be realized.

Now that the reader is familiar with a foundation of the invention, subsequent drawing figures and description will employ like reference numerals for analogous structure without the use of primes.

Figure 4:
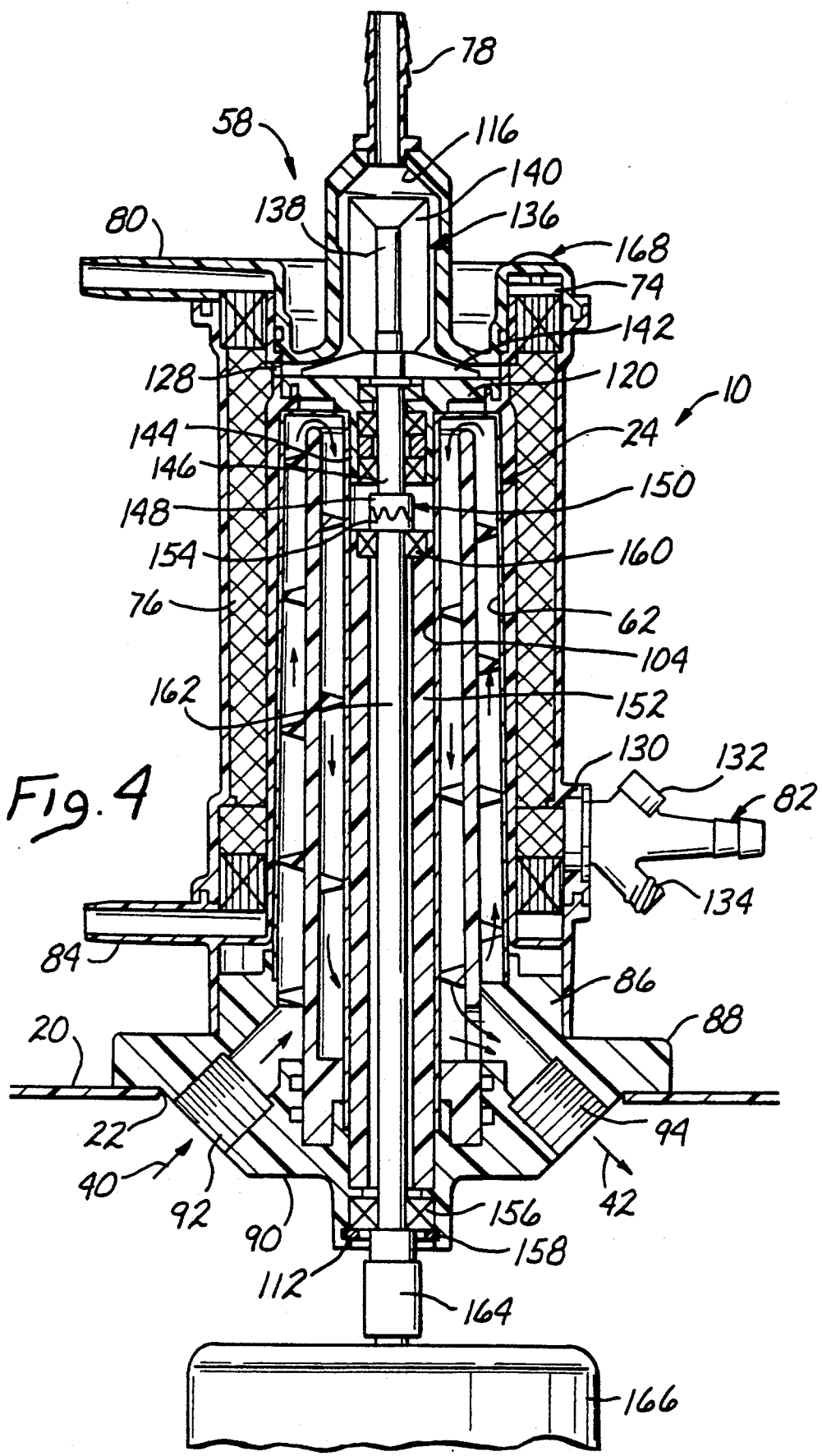
FIG. 4 is a side-sectional view of a blood oxygenator system according to an alternative embodiment of the present invention and having an axial pump.

Viewing FIG. 4, it will be seen that an alternative embodiment of the invention includes a disposable oxygenator/heat exchanger component 58 with a rotary pump 136. Pump 136 includes a pump rotor portion 138 journaled in chamber 116 and including an impeller 140 and a deflector disk 142 delivering blood flow to the transfer ports 128. The closure member 120 includes a neck 144 extending downwardly into the bore 104 of heat source component 24 and sealingly journaling a pump shaft 146 therein. Shaft 146 drivingly carries pump rotor portion 138. At its lower end, the shaft 146 defines one-half 148 of a dog coupling, referenced with numeral 150.

In order to drive the pump 136, the heat source component 24 now includes a bearing carrier sleeve 152 received in bores 96, 104 captively between the collar 110 and the other one-half 154 of the coupling 150. Bore 96 also carries a bearing 156 retained by snap ring 158 in retention groove 112. Bearing 156 cooperates with a bearing 160 at the top of sleeve 152 to journal a shaft 162. Shaft 162 carries at its upper end the coupling part 154, and at its lower end drivingly connects with a coupling 164 and drive motor 166. Operation of motor 166 rotates shaft 162, and via coupling 150 and shaft 146, drives pump 136. In addition to the pump 136, the oxygenator 58 also includes a pressure relief valve 168 opening from chamber 74 to vent gas-side pressure to atmosphere should this pressure exceed a desired level.

Those skilled in the pertinent art will recognize that the embodiment of FIG. 4 advantageously achieves integration of a blood oxygenation/heat exchanger having durable and disposable components with a blood pump and pump drive also having durable and disposable components in unit with the like components of the oxygenator/heat exchanger. Virtually no increase of blood priming volume is presented by the embodiment of FIG. 4 over that of FIGS. 2 and 3. In fact, the priming volume for the system is decreased compared to use of a separate blood pump and interconnecting tubes. After a surgical procedure, the oxygenator component 58 including pump 136 is discarded. Heat source component 24, with pump drive 150-166 is reusable.

Figure 5:
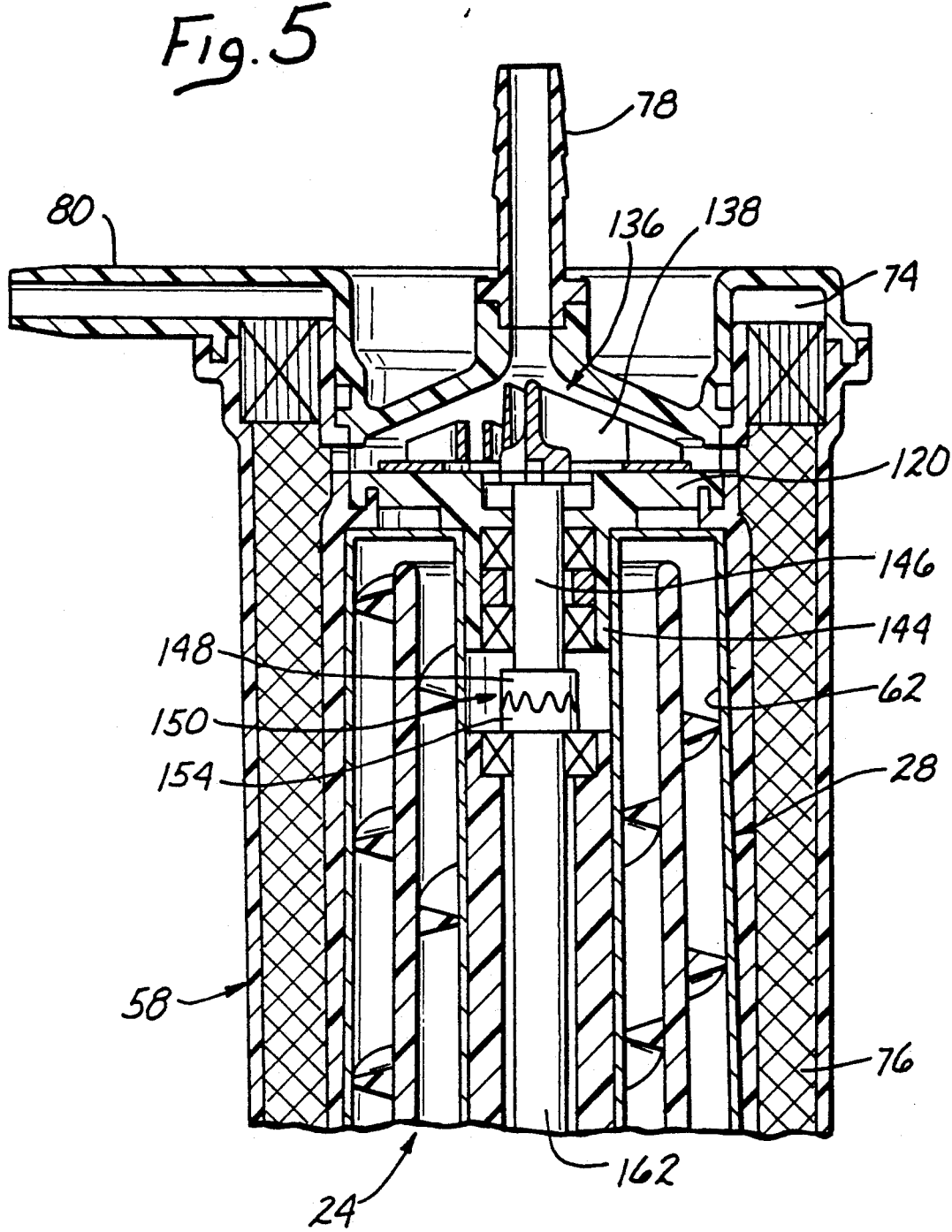
FIG. 5 is a fragmentary side-sectional view of a blood oxygenator system according to the present invention and having a centrifugal pump.

FIG. 5 depicts a fragmentary view of an alternative embodiment wherein pump 136 includes a pump rotor 138 of centrifugal type. In other respects, the oxygenator/heat exchanger component and heat source component 24 with pump drive 150-166 is the same as that depicted in FIG. 4. In fact, an oxygenator/heat exchanger according to either FIGS. 4 or 5 may be interchangeably used with the same heat source component 24 and pump drive 150-166. However, the centrifugal pump 136 of FIG. 5 may offer advantages in lower hemolysis or other blood damage.

Figure 6:
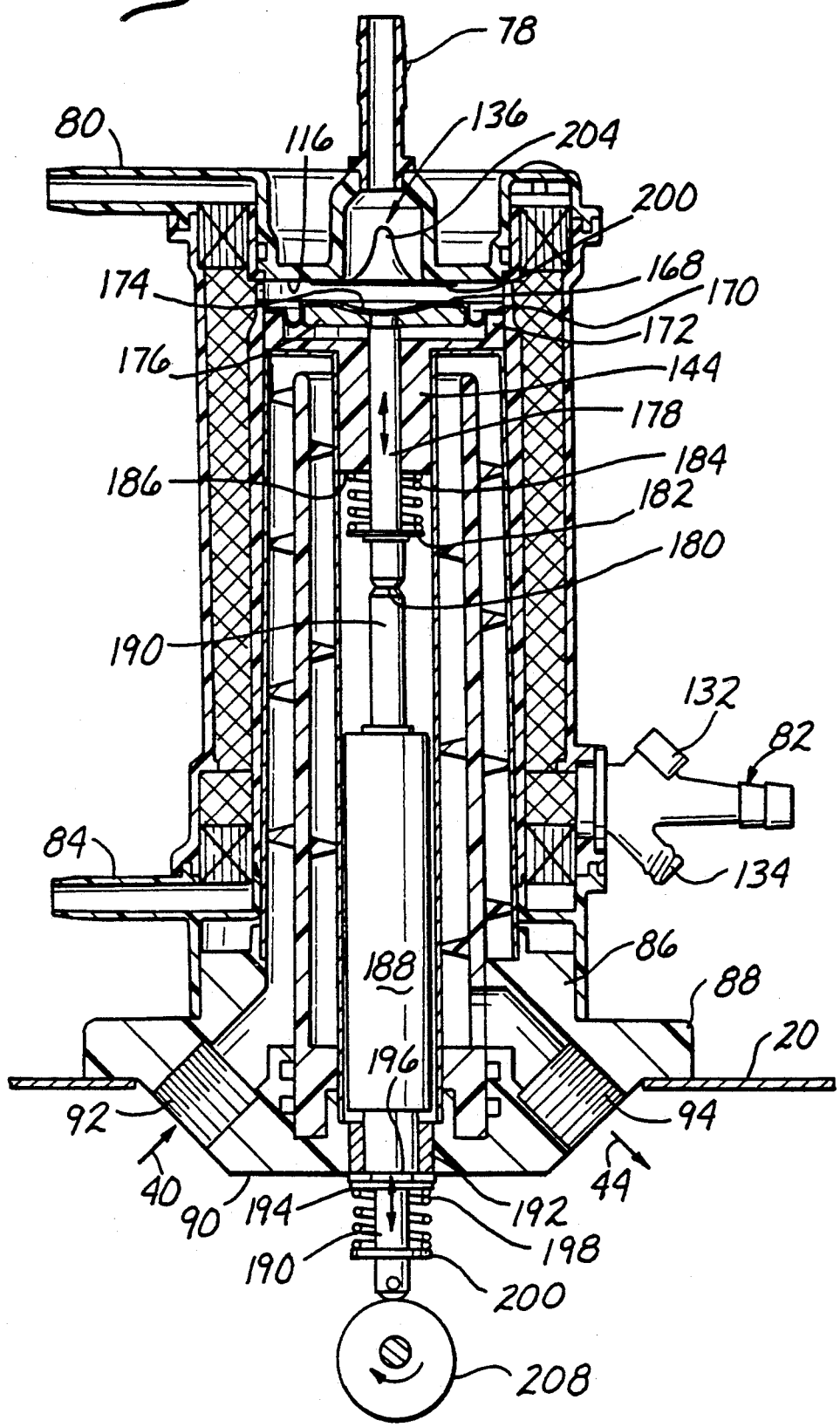
FIG. 6 is a side-sectional view of an alternative blood oxygenator system according to the present invention having a ventricular pump.

Yet another alternative embodiment of the invention is depicted by FIG. 6. As shown in FIG. 6, the blood pump 136 may include a ventricular rolling diaphragm member 168. The diaphragm 168 bounds the lower side of chamber 116, and is sealingly secured to a closure member 120 at mutual marginal edge portions 170, 172 of each. A central portion 174 of diaphragm 168 is supported on a disk-like member 176 reciprocable therewith. In order to drive the disk member 176 and central portion 174 vertically in reciprocation, the oxygenator/heat exchanger component 58 includes a neck 144 extending vertically into bore 104 of heat source component 24. Neck 144 reciprocally carries a central push rod 178 drivingly coupling at its upper end with disk 176. Rod 178 terminates at lower end surface 180, and carries a spring seat collar 182. A compression spring 184 extends between collar 182 and the lower end surface 186 of neck 144 to yieldably urge the rod 178, disk 176 and diaphragm 168 downwardly.

In place of the rotary pump drive components depicted and described with reference to FIGS. 4 and 5, the embodiment of FIG. 6 includes a push rod carrier 188 captively and reciprocally carrying a push rod 190. The carrier 188 engages collar 110 in bore 104 and is prevented from upward movement by a bushing 192 and snap ring 194, the latter engaging a groove 196 in the carrier 188. A compression coil spring 198 extends between the carrier 188 and a respective spring seat collar 200 to yieldably urge the push rod 190 downwardly into engagement with a rotational cam 202. Cam 202 is selectively rotational by a drive motor, not shown. Thus, when the cam 202 is rotated, push rod 190 is reciprocated. Proper operation of the pump drive may be verified visually without oxygenator component 58 in place on heat source component 28.

When the oxygenator component 28 is in place on the heat source component 58, as seen viewing FIG. 6, push rod 178 engages at surface 180 with push rod 190 to reciprocate therewith. Thus, diaphragm 168 is reciprocated to expand and contract chamber 116. Expansion of chamber 116 draws blood therein past a flapper-type unidirectional valve 204 disposed between inlet 78 and chamber 116. On the other hand, when chamber 116 contracts blood therein is pushed into chamber 74 via ports 128. Because the chamber 74 with membrane module 76 therein extends downwardly below pump 136, the descending column of liquid blood therein provides sufficient negative relative pressure that an outlet check valve is not required. Subsequent expansion of chamber 116 draws liquid in past valve 204 rather than drawing back significant liquid volume from chamber 74 via ports 128. Thus, hemolysis and other blood damage is further decreased by ventricular pump 136 because it requires no outlet check valve.

Figure 7:
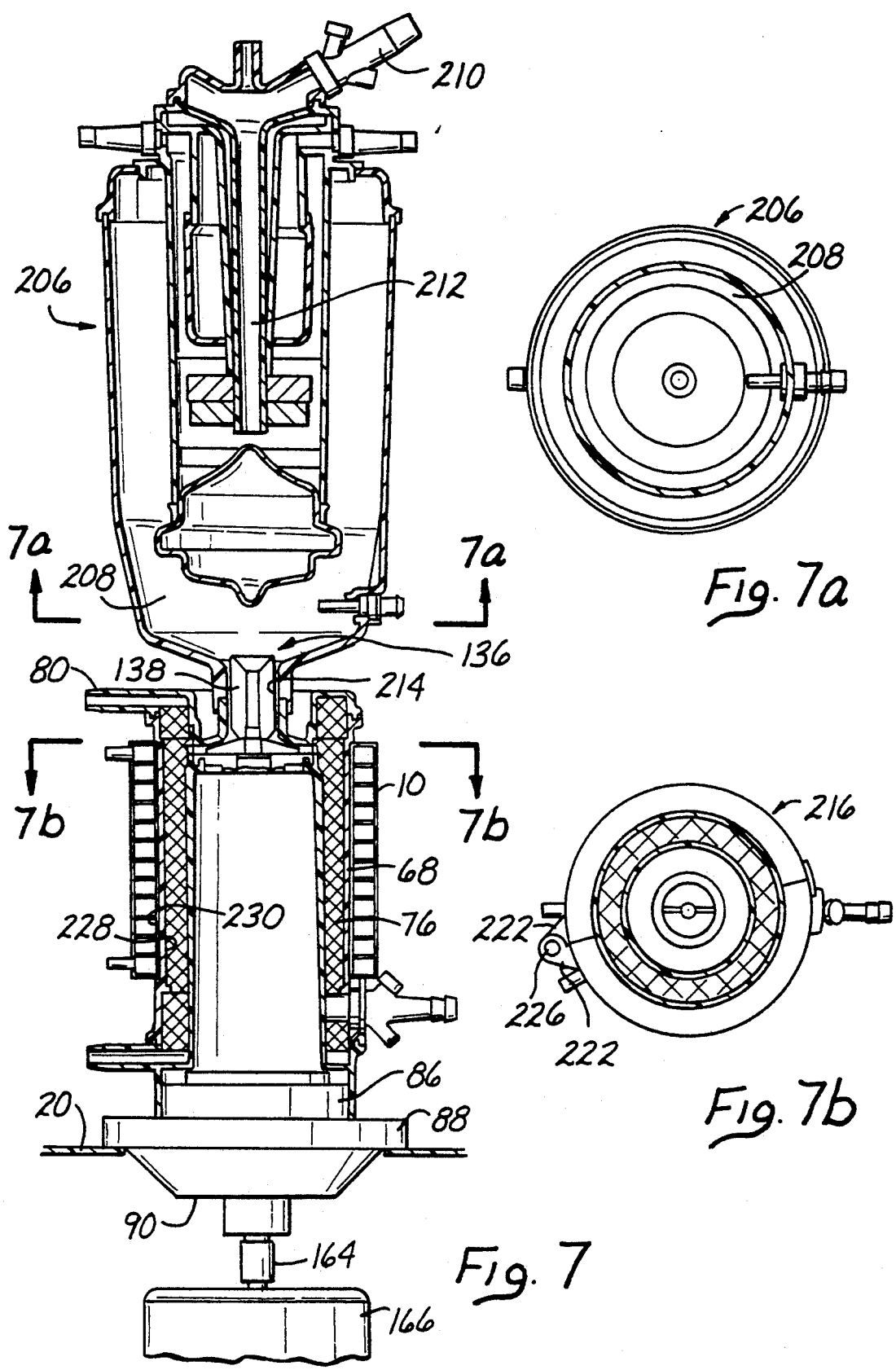

Still further, FIGS. 7, 7A and 7B depict another alternative embodiment of the invention wherein a disposable blood oxygenator/heat exchanger component is cooperable with the by now familiar durable heat source component, and includes a blood pump similar to that depicted and described by reference to FIG. 4. However, the disposable component also includes a rigid integral venous reservoir so arranged and cooperating with the blood pump that an outlet of the venous reservoir is the inlet to the blood pump. Also, FIG. 7 depicts an auxiliary heat source component in operative cooperation with the oxygenator/heat exchanger to substantially double the heat transfer capacity (heating or cooling) between the heat exchange medium and the blood being treated.

Turning now to FIG. 7A, a rigid venous reservoir 206 is depicted. This reservoir 206 includes a reservoir chamber 208 receiving patient blood via inlet 210 for flow down a channel 212. Subsequently, the blood is passed through the conventional materials and passageways to be received in chamber 208. From chamber 208, the reservoir defines a central outlet opening 214, which also defines the inlet to blood pump 136. In fact, the pump rotor 138 of pump 136 may extend upwardly into the chamber 208, if desired, in order to assist introduction of blood therefrom into the pump.

FIG. 7B depicts the lower portion of the oxygenator/heat exchanger, many features, components and operation of which will by now be familiar to the reader. However, the system 10 of FIGS. 7 also includes an auxiliary heat source device generally referenced with the numeral 216 and which will be better understood by reference to FIGS. 7B and perspective view FIG. 8. The auxiliary heat source component 216 includes a pair of clam-shell halves 218, 220 which are substantially identical c-shaped parts, each defining a hinge feature 222 at one edge. Part 220 is simply inverted with respect to part 218 so that the hinge features 222 interdigitate and are hingably connected by a hinge pin 226. Thus, the reader will understand that structural features and functions described with respect to one of the parts 218, 220 are duplicated in the other of these parts.

Figure 8:
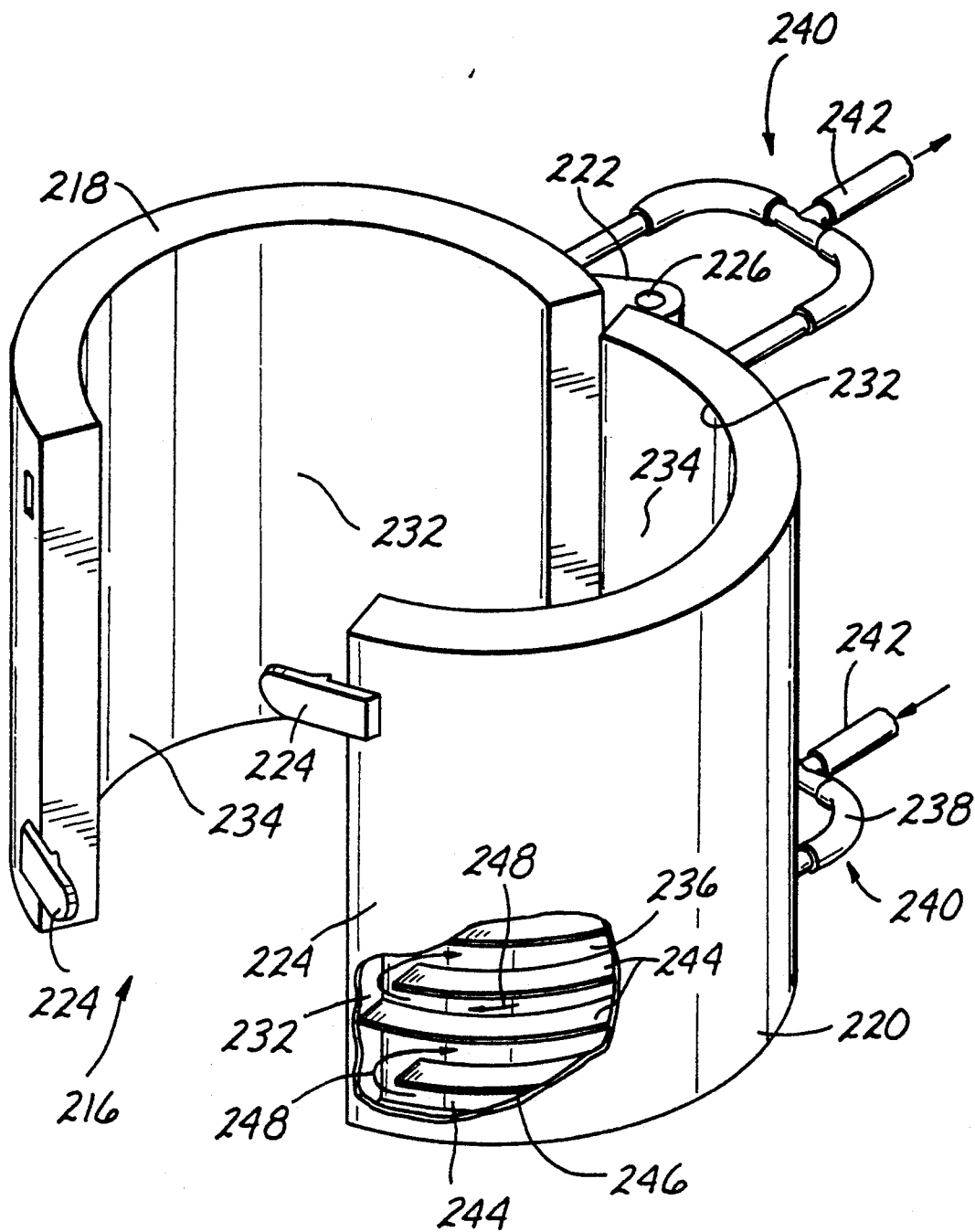
FIG. 8 provides a perspective view of an auxiliary heat source component seen in section in FIG. 7.

Viewing FIGS. 7B and 8, it is seen that the oxygenator/heat exchanger component includes an outer wall 68 having cylindrical inner and outer surfaces 228, 230, respectively. Of course surface 228 is vertically traversed by a flow of blood in oxygenator chamber 74 during operation of the system 10. The auxiliary heat source component 216 defines an radially inner heat transfer wall 232 with inner cylindrical surface 234 matching the cylindrical curvature of and engaging surface 230 in heat transfer relation. Viewing particularly FIG. 8, it is seen that each of the parts 218, 220 defines a portion of wall 232 with surface 234. In fact, each of the parts 218, 220 is hollow to define a chamber 236 for circulation of heat transfer fluid. In order to introduce and extract the heat transfer fluid to and from the chamber 236, the parts 218, 220 each define a pair of hose nipples (two of which are visible in FIG. 7B) to which a respective branch 238 of a pair of Y-shaped hoses 240 connects. The trunk 242 of the hoses 238 is connected via suitable valves (not shown) and T-connections to a respective one of the inlet or outlet ports 92, 94 of base 86. Thus, the auxiliary heat source, component 216 may remain permanently plumbed with heat source component 24 and its use, when indicated, requires simply its placement around the oxygenator/heat exchanger component 58, and the opening of the water supply and return valves.

Of course, the auxiliary heat source component 216 may also be used with the oxygenator/heat exchanger component 58 but without heat source component 24 by providing suitable alternative support for oxygenator 58, should such a use be desired.

In order to guide the fluid flow in chamber 236, each heat source component 218, 220 includes a plurality of cooperating arcuate fins 244 which are alternately adjacent and spaced from the ends of the chambers 236. Thus, fluid circulation in the chambers 236 follows a serpentine flow path 246, from bottom to top as depicted by arrows 248.

Those skilled in the pertinent art will recognize that the present invention provides a modular selectively-configured blood oxygenator/heat exchanger component which is disposable and which is cooperable in heat transfer with a separate durable heat source component to be supported thereon. The heat source component may be permanently plumbed in an operating room for convenience and to reduce clutter. Selectively, the oxygenator/heat exchanger component may include a blood pump driven by a durable pump drive carried with the heat source, may include a venous reservoir, and may cooperate in heat transfer relation with an optional auxiliary heat source component also permanently plumbed, if desired. The prospective advantages of reduced blood priming volume, redundant separation of blood and heat transfer media, reduced time burden and chance of error in set up, decreased risk of blood contact, decreased retained blood volume after surgery, low cost disposability of blood-contacted components, reduced blood-contacted surface area, decreased blood damage and foreign surface contact which could cause immunoreactive response, and selection of blood pump configuration while retaining an advantageous and short blood flow path in the apparatus with retention of the advantage of reduced priming volume, are all realized by the present invention.

I claim:

1. A method for oxygenating blood, the method comprising the steps of:
  supporting a heat source component defining a heat exchange surface on a support such that the heat source component extends at least partly upwardly;
  placing a blood oxygenator/heat exchanger unit over the heat source component such that the latter supports the blood oxygenator unit;
  defining a blood boundary wall of said oxygenator/heat exchanger unit which on one side defines a blood boundary heat transfer surface and outwardly exposes an outer heat transfer surface, engaging said heat exchange surface and said outer heat transfer surface in heat transfer relation;
  passing a heat exchange medium through the heat source component; and
  passing blood through the blood oxygenator unit and along said blood boundary heat transfer surface such that blood makes no contact with the heat source component.

2. The method of claim 1 further including the step of defining with said outer heat transfer surface a frustoconical recess, and bounding with said heat exchange surface a frustoconical shape receivable into said recess in heat exchange supporting relationship with said blood oxygenator/heat exchanger component.

3. The method of claim 1 further comprising the step of passing blood into the oxygenator unit from a pump located adjacent the top of the blood oxygenator unit.

4. The method of claim 3 further comprising the step of driving a blood pump with a blood pump motor through a drive shaft passing through an interior portion of the heat source component.

5. The method of claim 3 further including passing blood from an upper venous reservoir integral with said blood oxygenator unit downwardly therethrough.

6. The method of claim 1 further including the step of transferring heat between blood in the oxygenator unit and a separate heat source component circumscribing said oxygenator component.

7. The method of claim 6 further including the steps of defining with said outer heat transfer surface a right circular cylindrical shape, and defining said separate heat source component with a radially inwardly disposed heat exchange surface engageable with said heat transfer surface.

8. The method of claim 7 wherein said transferring step includes defining said separate heat source component to include a pair of C-shaped portions each defining a radially inwardly disposed part of said radially inwardly disposed heat exchange surface, and closing said pair of C-shaped portions around said oxygenator/heat exchanger unit to engage said heat exchange surface with said outer heat transfer surface.

9. A blood oxygenator/heat exchange apparatus comprising a chambered blood oxygenator component having a boundary wall bounding said chamber and defining blood inlet and outlet ports and oxygenating gas inlet and outlet ports for respective flow of blood and oxygenating gas through said chamber, means disposed in said chamber for effecting oxygen take up by blood flowing through said chamber, said boundary wall also defining a heat transfer surface exposed externally of said chamber and said blood flow traversing said boundary wall inwardly of said heat transfer surface; a separate heat source component defining an outer wall surface conformal to said heat transfer surface and engageable therewith in heat transfer relation, said heat source component and said oxygenator/heat exchanger component being cooperable to engage said outer wall surface and said heat transfer surface in heat transfer relation thereby to effect heat transfer between said heat source component and blood within said chamber via said boundary wall, whereby said oxygenator/heat exchanger component is also separable from said heat source component.

10. The blood oxygenator/heat exchanger apparatus of claim 1 wherein said heat source component defines a cavity therein bounded by an outer wall, said outer wall defining inlet and outlet ports for flow of fluid heat transfer media through said cavity and also defining said outer wall surface, each of said outer wall and said boundary wall sealingly separating said heat transfer media from said blood, whereby redundant separation of said heat transfer media from said blood is provided by said blood oxygenator/heat exchanger.

11. The blood oxygenator/heat exchanger apparatus of claim 9 wherein said heat source component is supported upon a base, said blood oxygenator/heat exchanger component being supported on said heat source component.

12. The blood oxygenator/heat exchanger apparatus of claim 11 wherein said heat source component defines an upwardly extending housing portion outwardly bounded by said outer wall, said oxygenator/heat exchanger component defining an upwardly opening cavity inwardly bounded by said boundary wall, said oxygenator/heat exchanger component being receivable upon said heat source component to be supported thereby and to engage said boundary wall surface in heat transfer relation with said outer wall surface.

13. The blood oxygenator/heat exchanger apparatus of claim 12 wherein said upwardly extending housing portion is slightly frustoconical increasing in diameter in a downward direction, said cavity being also of frustoconical shape matching said housing portion to engage said boundary wall surface and said outer wall surface in heat exchange relation when said oxygenator/heat exchanger component is received in supported relation upon said heat source component.

14. The blood oxygenator/heat exchanger apparatus of claim 13 wherein said chamber is annular to extend vertically, said boundary wall defining a radially inner wall of said chamber and a radially outer wall of said cavity, whereby said annular cavity circumscribes said heat source component.

15. The blood oxygenator/heat exchanger apparatus of claim 14 wherein said blood inlet port communicates with said annular chamber near the upper extent thereof while said blood outlet port communicates from a lower extent of said chamber, blood flowing from said inlet to said outlet forming a descending liquid column flowing at least partially by gravity assistance.

16. The blood oxygenator/heat exchanger apparatus of claim 15 wherein said oxygenator/heat exchanger component further includes a central chamber disposed above said heat source component and communicating blood from said blood inlet port to said chamber, means disposed in said central chamber for pumping blood from said inlet through said chamber.

17. The blood oxygenator/heat exchanger apparatus of claim 8 wherein said blood pumping means includes an axial-flow rotary pump.

18. The blood oxygenator/heat exchanger apparatus of claim 16 wherein said blood pumping means includes a centrifugal-flow rotary pump.

19. The blood oxygenator/heat exchanger apparatus of claim 16 wherein said blood pumping means includes a reciprocable member bounding said central chamber to vary the volume thereof in response to reciprocation of said member.

20. The blood oxygenator/heat exchanger apparatus of claim 16 wherein said heat source component defines a vertical central passage aligned with said central chamber, and pump drive means disposed in said central passage for driving cooperation with said blood pump means.

21. The blood oxygenator/heat exchanger apparatus of claim 20 wherein said pump drive means includes a rotational drive shaft drivingly cooperable with said pump means, and said drive shaft being driven by a motor disposed below said heat source component.

22. The blood oxygenator/heat exchanger apparatus of claim 20 wherein said pump drive shaft; and means includes a vertically reciprocable drive shaft, and means associated with said heat source component for reciprocating said reciprocable drive shaft.

23. The blood oxygenator/heat exchanger apparatus of claim 9 wherein said boundary wall of said oxygenator/heat exchanger component also defines an outer heat transfer surface circumscribing said chamber, an auxiliary heat source component defining a heat exchange surface conformal with said outer heat transfer surface and engageable therewith in heat exchange relation to transfer heat between blood within said chamber and said auxiliary heat source component.

24. The blood oxygenator/heat exchanger apparatus of claim 23 wherein said auxiliary heat source component is of clam-shell construction having a pair of parts hingedly connected and closing cooperatively about said oxygenator/heat exchanger component.

25. A chambered disposable blood oxygenator/heat exchanger component, said component comprising: a blood boundary wall bounding said chamber and including concentric elongate vertically extending radially inner and radially outer boundary wall portions radially spaced apart to bound said chamber in annular configuration therebetween, upper and lower radially extending boundary wall portions cooperating with said inner and outer wall positions to bound said chamber, said boundary wall defining blood inlet and outlet ports and oxygenating gas inlet and outlet ports for respective flow of blood and oxygenating gas through said chamber, said radially inner wall portion including a heat transfer surface portion bounding a slightly frustoconical cavity open downwardly and tapering with decreasing diameter in an upward direction, and means for effecting oxygen uptake by blood flowing in said chamber, whereby said oxygenator/heat exchanger is supportable upon a eat source component receivable into said cavity to engage a heat exchange surface thereof with said heat transfer surface.

26. The chambered disposable blood oxygenator/heat exchanger component of claim 25 wherein said oxygenator/heat exchanger component also includes means for pumping blood through said chamber.

27. The chambered disposable blood oxygenator/heat exchanger component of claim 26 wherein said blood pumping means in selected from the group including axial-flow, centrifugal-flow, and variable-volume ventricular pumps.

28. The chambered disposable blood oxygenator/heat exchanger component of claim 27 also including disposable pump drive apparatus drivingly cooperable with durable pump drive apparatus carried by said heat source component.

29. The chambered disposable blood oxygenator/heat exchanger component of claim 28 further including integral structure defining a venous reservoir communicating at an outlet thereof with said blood pumping means.

30. The chambered disposable blood oxygenator/heat exchanger component of claim 25 wherein said oxygenator/hear exchanger component also includes a radially outer cylindrical heat transfer surface portion also defined by said boundary wall, whereby said radially outer heat transfer surface portion is engageable by an auxiliary heat source component having a heat exchange surface engageable therewith.

31. A blood oxygenator/heat exchanger comprising a chambered housing component inwardly bounding a blood oxygenation chamber and outwardly defining a recess bounded by a heat transfer wall having a heat transfer surface, said heat transfer wall inwardly being traversed by a flow of blood in heat transfer relation therewith; a heat source component receivable into and generally conformal with said recess, said heat source component defining an outwardly disposed heat exchange surface engageable with said heat transfer surface.

32. The blood oxygenator/heat exchanger of claim 31 wherein said recess in of frustoconical shape tapering inwardly with decreasing diameter, said heat transfer component outwardly being of frustoconical shape matching said recess.

33. The blood oxygenator/heat exchanger of claim 32 wherein said heat transfer component is carried upon and extends upwardly from a base, said oxygenator/heat exchanger component being receivable upon said heat transfer component for support thereby.

34. The blood oxygenator/heat exchanger of claim 31 wherein said oxygenator/heat exchanger also includes a blood pump, said oxygenator/heat exchanger component and said heat source component cooperatively defining separable drive means for driving said pump.

35. The blood oxygenator/heat exchanger of claim 34 wherein said pump drive means includes said heat source component defining a passage therethrough, a pump drive shaft received and movable in said passage to drive said pump.

36. The blood oxygenator/heat exchanger of claim 35 wherein said oxygenator/heat exchanger component defines a closed recess end, said blood pump being disposed at said closed recess end in alignment with said heat source component and said through passage thereof.

37. The blood oxygenator/heat exchanger of claim 34 wherein said extending/heat source component defines a neck portion including said neck portion movably carrying a first pump drive shaft captively retained with said oxygenator/heat exchanger component, and said pump drive means also including a second pump drive shaft captively retained by said heat source component and drivingly but separably cooperable with said first drive shaft to power said pump.

38. The blood oxygenator/heat exchanger of claim 31 wherein said blood oxygenator/heat exchanger further includes a venous reservoir defining a part of said chamber and disposed upwardly of said blood oxygenator chamber thereof.

39. The blood oxygenator/heat exchanger of claim 33 also including a second heat source component receivable about said blood oxygenator/heat exchanger component.

* * * * *